United States Patent
Hao et al.

Patent Number: 5,969,154
Date of Patent: Oct. 19, 1999

[54] LIQUID CRYSTALLINE DIKETOPYRROLOPYRROLES

[75] Inventors: Zhimin Hao, Marly; Abul Iqbal, Arconciel; Nancy Tebaldi, Matran, all of Switzerland; Klaus Praefcke, Berlin, Germany

[73] Assignee: Ciba Specialty Chemicals Corporation, Tarrytown, N.Y.

[21] Appl. No.: 08/988,419

[22] Filed: Dec. 10, 1997

[30] Foreign Application Priority Data

Dec. 10, 1996 [CH] Switzerland .............................. 3026.96
Dec. 10, 1996 [CH] Switzerland .............................. 3027.96

[51] Int. Cl.$^6$ ...................... C07D 487/04; C07D 317/12; C07D 319/06
[52] U.S. Cl. ...................... 548/453; 548/467; 548/512; 548/515; 548/517; 549/369; 549/373; 549/374; 549/430; 549/451; 549/453; 549/415; 549/416; 564/248; 564/272; 564/273; 252/299.61; 252/299.62
[58] Field of Search ............................................. 548/453

[56] References Cited

U.S. PATENT DOCUMENTS

| | | | |
|---|---|---|---|
| 4,579,949 | 4/1986 | Rochat et al. | 546/167 |
| 4,585,878 | 4/1986 | Jost et al. | 548/453 |
| 4,659,775 | 4/1987 | Pfenninger et al. | 524/92 |

OTHER PUBLICATIONS

K. Praefcke et al., Liquid Crystals, 1998, vol. 24, No. 1, pp. 153–156.
J. Am. Chem. Soc. (1982), 104, pp. 5245–5247 Piechocki et al.
Edman, Peter et al., J. Phys. Chem., 99, pp. 8504–8509 (1995).

*Primary Examiner*—Johann Richter
*Assistant Examiner*—Jane C. Oswelki
*Attorney, Agent, or Firm*—Kevin T. Mansfield; Jacob M. Levine

[57] ABSTRACT

A liquid crystalline compound of formula

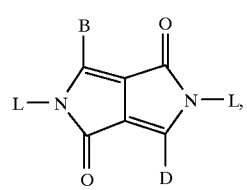
(I)

wherein

B and D are each independently of the other $C_6$–$C_{24}$alkyl,

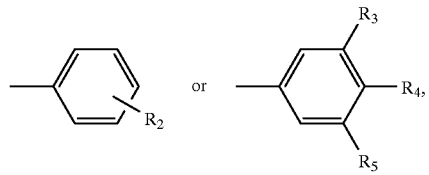

L is

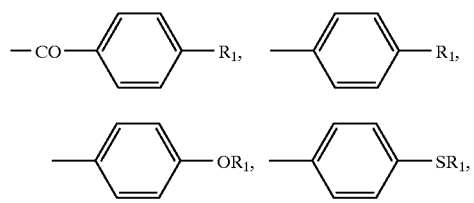

methyl or $C_{10}$–$C_{18}$alkyl, wherein $R_1$ is $C_4$–$C_{18}$alkyl, with the proviso that when L is methyl, at least one of B and D is $C_6$–$C_{24}$ alkyl;

$R_2$ is hydrogen, $C_1$–$C_4$alkyl, $C_1$–$C_4$alkoxy, halogen, cyano or nitro, $R_3$, $R_4$ and $R_5$ are each independently of one another hydrogen, OR6, SR6, SeR6, —NHR6, —NR6R7,

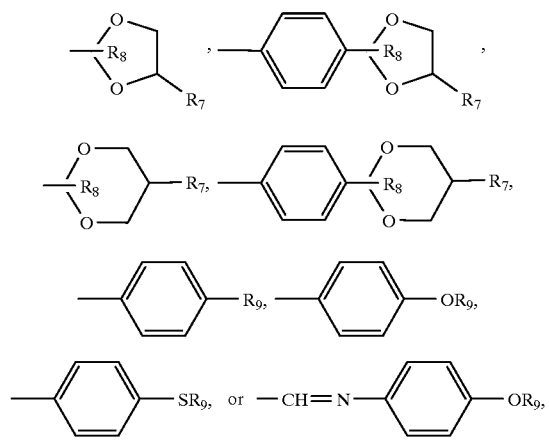

with the proviso that at least one of R3, R4 and R5 is not hydrogen, R6 is $C_7$–$C_{37}$alkyl, $C_7$–$C_{37}$alkylene or $C_5$–$C_{18}$alkyl which is interrupted by 1 to 6 hetero atoms selected from the group consisting of O, S and N, R7 is hydrogen or R9, R8 is hydrogen or $C_1$–$C_4$alkyl, and R9 is $C_1$–$C_{12}$alkyl, $C_2$–$C_{12}$alkylene or $C_3$–$C_{12}$alkyl which is interrupted by 1 to 6 hetero atoms selected from the group consisting of O, S and N.

16 Claims, No Drawings

LIQUID CRYSTALLINE DIKETOPYRROLOPYRROLES

The present invention relates to novel liquid crystalline N-substituted 1,4-diketo-3,6-diarylpyrrolo[3,4-c]pyrroles, 1,4-diketo-3,6-dialkylpyrrolo[3,4-c]pyrroles and 1,4-diketo-3-alkyl-6-arylpyrrolo[3,4-c]pyrroles.

1,4-Diketopyrrolo[3,4-c]pyrroles, including the 1,4-diketo-3,6-dialkylpyrrolo[3,4-c]pyrroles disclosed in U.S. Pat. No. 4,659,775, have been known for some years as excellent pigments. N-substituted 1,4-diketopyrrolo[3,4-c] pyrroles, which are excellently suitable as pigments, are disclosed in U.S. Pat. No. 4,585,878.

However, except in very rare cases liquid crystalline compounds, such as the phthalocyanine described in J. Amer. Chem. Soc. 104, 5245–5247 (1982), are colourless and must be used together with chromophoric substances to give coloured liquid crystalline phases.

Novel coloured N-substituted 1,4-diketopyrrolo[3,4-c] pyrroles have now been found which, very surprisingly, have a liquid crystalline character.

Accordingly, this invention relates to a compound of formula

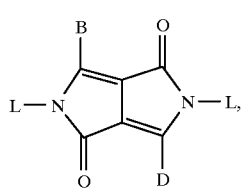

(I)

wherein

B and D are each independently of the other $C_6$–$C_{24}$alkyl,

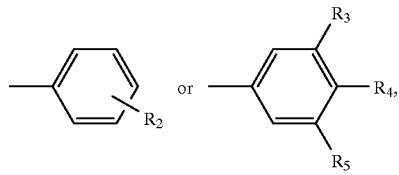

L is

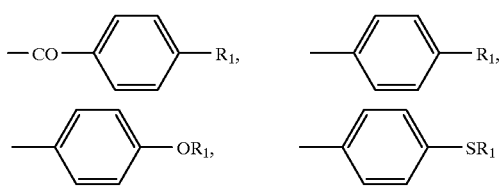

$C_1$–$C_{37}$alkyl, $R_1$ is $C_4$–$C_{18}$alkyl, $R_2$ is hydrogen, $C_1$–$C_4$alkyl, $C_1$–$C_4$alkoxy, halogen, cyano or nitro, $R_3$, $R_4$ and $R_5$ each independently of one another hydrogen, $OR_6$, $SR_6$, $SeR_6$, —$NHR_6$, —$NR_6R_7$,

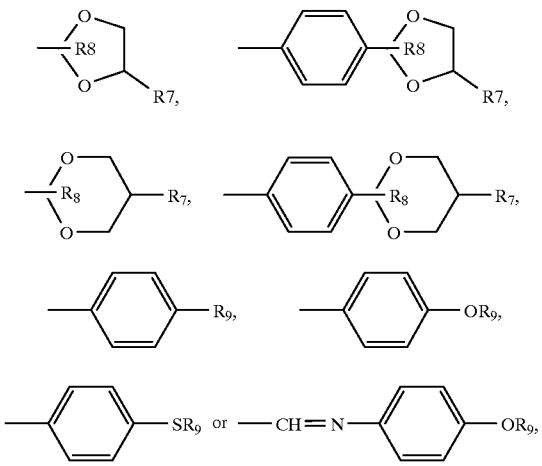

with the proviso that at least one of $R_3$, $R_4$ and $R_5$ is not hydrogen, $R_6$ is $C_7$–$C_{37}$alkyl, $C_7$–$C_{37}$alkylene, or $C_5$–$C_{18}$alkyl which is interrupted by 1 to 6 hereto atoms selected from the group consisting of O, S and N, $R_7$ is hydrogen or $R_9$, $R_8$ is hydrogen or $C_1$–$C_4$alkyl, and $R_9$ is $C_1$–$C_{12}$alkyl, $C_2$–$C_{12}$alkylene, or $C_3$–$C_{12}$alkyl which is interrupted by 1 to 6 hereto atoms selected from the group consisting of O, S and N.

Alkyl or alkylene may be straight-chain, branched, monocyclic or polycyclic.

Accordingly, $C_1$–$C_{37}$alkyl is, for example, methyl, ethyl, n-propyl, isopropyl, n-butyl, sec-butyl, isobutyl, tert-butyl, cyclobutyl, n-pentyl, 2-pentyl, 3-pentyl, 2,2-dimethylpropyl, cyclopentyl, cyclohexyl, n-hexyl, n-octyl, 1,1,3,3-tetramethylbutyl, 2-ethylhexyl, nonyl, trimethylcyclohexyl, decyl, menthyl, thujyl, bornyl, 1-adamantyl, 2-adamantyl, dodecyl, tetradecyl, hexadecyl, octadecyl, eicosyl, heneicosyl, docosyl or tetracosyl. $C_1$–$C_{37}$Alkyl is usually preferably methyl, straight-chain $C_{10}$–$C_{24}$alkyl or $$-\begin{array}{c} R_{10} \\ | \\ R_{10}' \end{array}$$

wherein $R_{10}$ and $R_{10}'$ are each independently of the other straight-chain $C_{10}$–$C_{18}$alkyl. $C_1$–$C_{37}$Alkyl is usually particularly preferably methyl, straight-chain $C_{10}$–$C_{18}$alkyl or $$-\begin{array}{c} R_{10} \\ | \\ R_{10}' \end{array},$$

wherein $R_{10}$ and $R_{10}'$ are straight-chain $C_{10}$–$C_{14}$alkyl.

$C_7$–$C_{37}$Alkylene is mono- or polyunsaturated $C_7$–$C_{37}$alkyl.

$C_5$–$C_{18}$Alkyl which is interrupted by 1 to 6 hetero atoms selected from the group consisting of O, S and N is typically —$(CH_2CH_2O)_n$—$R_{11}$, —$(CH_2CH(CH_3)O)_n$—$R_{11}$, —$(CH_2CH_2N(CH_2CH_2OR_{11})_2$, 2-morpholylethyl or 2-tetrahydropyranyl, wherein n is a number from 1 to 6, and $R_{11}$ is $C_1$–$C_{12}$-alkyl. In general, interrupting a chain by hetero atoms has substantially the same effect as extending its length by the same number of carbon atoms.

Halogen is typically chloro, bromo or fluoro, preferably chloro.

L is preferably methyl, straight-chain $C_{10}$–$C_{18}$alkyl or

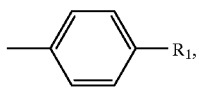

most preferably methyl or straight-chain $C_{10}$–$C_{18}$alkyl. If B is $C_6$–$C_{24}$alkyl, then L is particularly preferably methyl.

B and D are preferably identical. B and D are particularly preferably straight-chain $C_6$–$C_{10}$-alkyl,

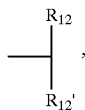

wherein $R_{12}$ and $R_{12}'$ are straight-chain $C_{10}$–$C_{14}$alkyl,

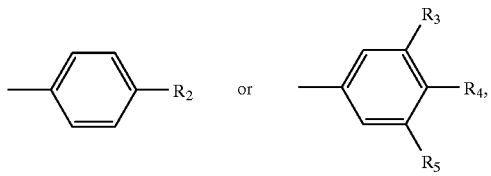

very particularly preferably

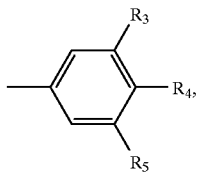

wherein $R_2$, $R_3$, $R_4$ and $R_5$ have the meanings cited above.

$R_1$ is preferably $C_6$–$C_{12}$alkyl.

$R_2$ is preferably halogen, cyano or nitro, particularly preferably halogen.

$R_3$, $R_4$ or $R_5$ other than hydrogen is preferably $OR_6$, $SR_6$,

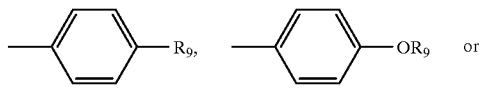

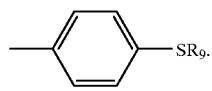

$R_6$ is preferably straight-chain $C_{10}$–$C_{24}$alkyl or

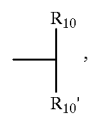

wherein $R_{10}$ and $R_{10}'$ are each independently of the other straight-chain $C_{10}$–$C_{18}$alkyl, particularly preferably straight-chain $C_{10}$–$C_{18}$alkyl or

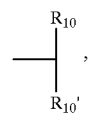

wherein $R_{10}$ and $R_{10}'$ are straight-chain $C_{10}$–$C_{14}$alkyl.

$R_7$ is preferably $C_1$–$C_{12}$alkyl.

$R_8$ is preferably hydrogen.

$R_{11}$ is preferably methyl or ethyl.

Compounds of particular interest are 1,4-diketopyrrolo[3,4-c]pyrroles of formula IIa, IIb, IIc or IId,

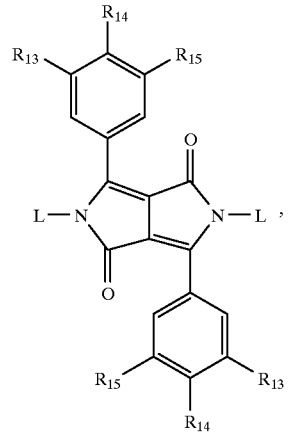

(IIa)

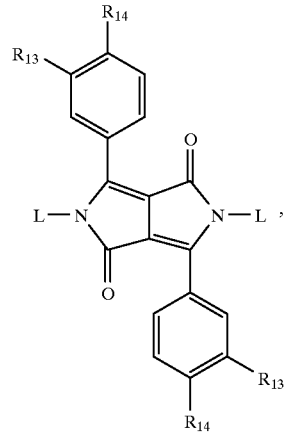

(IIb)

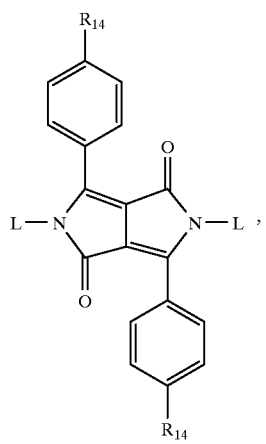
(IIc)

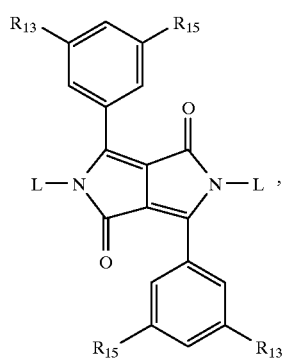
(IId)

wherein $R_{13}$, $R_{14}$ and $R_{15}$ are each independently of one another $OR_6$, $SR_6$, $SeR_6$, —$NHR_6$, —$NHR_7$,

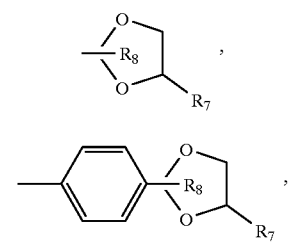

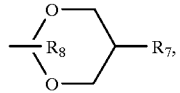

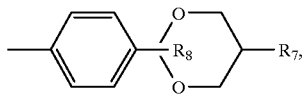

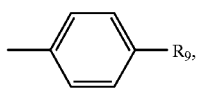

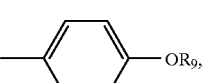

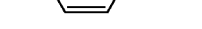

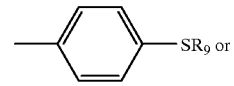

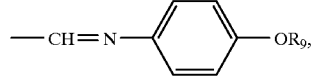

and L, $R_6$, $R_7$, $R_8$ and $R_9$ have the meaning cited above.

Prefrred 1,4-diketopyrrolo[3,4-c]pyrroles are those of formula IIa, IIb, IIc or IId, wherein L is methyl, straight-chain $C_{10}$–$C_{18}$alkyl or

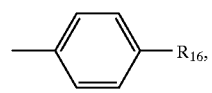

$R_6$ is straight-chain $C_{10}$–$C_{18}$alkyl, and $R_{16}$ is straight-chain $C_6$–$C_{12}$alkyl and, in particular, those wherein $R_{13}$, $R_{14}$ and $R_{15}$ are each independently of one another $OR_6$, $SR_6$,

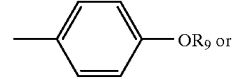

The inventive 1,4-diketopyrrolo[3,4-c]pyrroles of formula I, wherein B and D are identical aryl groups, can be prepared in general analogy to commonly known methods, for example by reacting 1 mol of dialkyl succinate with 2 mol of a nitrile of formula

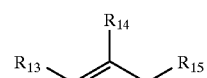
(III)

in accordance with the process described in U.S. Pat. No. 4,579,949 to a diketopyrrolopyrrole of formula

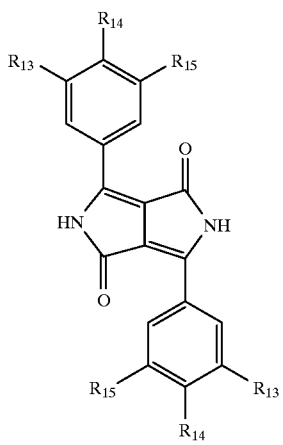

(IV)

which is then reacted with 2 mol of a compound of formula L—Y (V), wherein Y is a leaving group, such as chloro, bromo, iodo or toluenesulfonyl, as is described in U.S. Pat. No. 4,585,878.

The inventive 1,4-diketopyrrolo[3,4-c]pyrroles of formula I, wherein B and D are different groups or identical alkyl groups, can be prepared in general analogy to commonly known methods, for example by reacting a pyrrolinone of formula

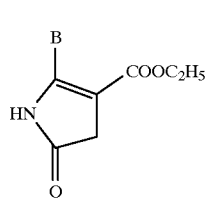

(VI)

with a nitrile of formula D-CN (VII) at a molar ratio of 1:1 in accordance with the process described in U.S. Pat. No. 4,659,775 to a diketopyrrolopyrrole of formula

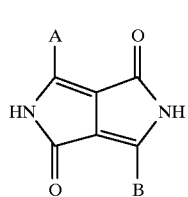

(VIII)

which is then reacted with 2 mol of a compound of formula L—Y (V), as is described in U.S. Pat. No. 4,585,878.

The compounds of formula III, V, VI and VII are compounds which are known per se. Should any of them still be novel they can be prepared by generally known methods.

Surprisingly, the novel 1,4-diketopyrrolo[3,4-c]pyrroles meet the demands placed on the liquid crystalline compounds with the additional advantage that they have inherent colour which, depending on the structure (in particular depending on groups B and D), can range from yellow to orange, red and blueish red. They are therefore excellently suitable for the manufacture of optical devices having liquid crystalline properties, no admixture of additional colourants being required. Accordingly, this invention also relates to the use of a compound of formula I for the manufacture of optical devices having liquid crystalline properties.

Optical devices having liquid crystalline properties are, for example, liquid crystalline displays which, depending on the applied electrical voltage, have different colours or may also be colourless. Preferred liquid crystalline displays are those, wherein a great number of points or segments can be controlled individually, i.e. screens. Liquid crystalline colour screens are particularly preferred.

Accordingly, this invention also relates to an optical device having liquid crystalline properties, which comprises a compound of formula I.

The inventive compounds of formula I can be used singly. However, they can also be used in mixtures with other compounds of formula I, for example as binary or ternary mixtures. It is also possible, however, to combine the novel compounds of formula I as components with compounds of different chemical structure which are known to have a liquid crystalline state. By mixing different liquid crystalline compounds with each other and/or with additives known per se, the physical properties of the liquid crystalline phase can be influenced, in particular the order parameter, the viscosity and the temperature range in which liquid crystallinity occurs. The inventive compounds of formula I can be used in mixtures even in cases where the pure compounds of formula I do not clearly show a liquid crystalline state.

This invention therefore also relates to a liquid crystalline phase, comprising 0.1 to 100% by weight, based on the entire liquid crystalline phase, of a compound of formula I. The liquid crystalline phase preferably comprises at least 1% by weight, particularly preferably at least 10% by weight, very particularly preferably at least 40% by weight, based on the entire liquid crystalline phase, of a compound of formula I. The liquid crystalline phase most preferably consists essentially of 1 to 3 liquid crystalline components.

The inventive compounds are also excellently suited as liquid crystal dyes for improving the colour contrast of known, coloured or preferably colourless liquid crystals. The resulting coloured liquid crystalline phases have improved properties, as compared with liquid crystalline phases coloured by known liquid crystal dyes [see P. Gregory, High Technology Applications of Organic Colorants, Chapter 1 (Plenum Press, New York & London 1991), and therein cited references)]; especially the order parameter and the light stability are high.

Depending on the structure, in particular on the length of L, on the degree of branching of B and D, and/or on the nature of $R_{13}$, $R_{14}$ and $R_{15}$ in formulae IIa to IId, the inventive liquid crystalline compounds of formula I are calamitic or discotic liquid crystals. Calamitic liquid crystals are promoted by short L (for example methyl) and/or in particular by rectilinear and unbranched B and D (for example 4-(n-decyloxy)phenyl or (4'-alkoxy-biphenyl)-4-yl). Calamitic liquid crystals are preferably of formula IIa, IIb or IIc, wherein L is methyl and/or $R_{14}$ is unsubstituted and/or substituted biphenyl-4-yl. Discotic liquid crystals on the other hand are promoted by long L (for example straight-chain dodecyl) and/or in particular by highly branched B and D (for example 3,4,5-tri(n-decyloxy)phenyl). Discotic liquid crystals are preferably of formula IIa, IIb or IId, wherein L is $C_{10}$–$C_{18}$alkyl and/or $R_{13}$ and $R_{15}$, are $OR_6$, $SR_6$, $NHR_6$ or $NR_6R_7$.

Depending on the structure and temperature, a columnar, nematic or smectic mesophase may be found. Preferred liquid crystalline compounds are those of formula I having a nematic phase, particularly preferably a nematic as well as a smectic phase. Those liquid crystalline compounds are preferred which have a high enthalpy change upon transition from the crystalline to the liquid crystalline state.

The following examples illustrate the invention. Unless otherwise stated, alkyl is n-alkyl and the assignment of the mesophase is not always clear:

EXAMPLE 1 a) A solution consisting of 77.55 g (0.3 mol) of 1-hexadecanethiol in 50 ml of N,N-dimethylacetamide is added, with stirring, to a suspension consisting of 41.27 g (0.3 mol) of 4-chlorobenzonitrile and 58.05 g (0.42 mol) of potassium carbonate (anhydrous) in 200 ml of N,N-dimethylacetamide. After heating this mixture under nitrogen to 120° C., it is stirred for 18 hours at this temperature and then cooled to room temperature and charged with 1 l of water. The mixture is then filtered and the filtrate is washed with water until it is neutral. The product is dried at 60° C./160 mbar.

107.1 g (99.3% of theory) of 4-(hexadecylthio) benzonitrile (white powder) are obtained.

| Analysis: | C | H | N | S |
|---|---|---|---|---|
| calcd.: | 76.82% | 10.36% | 3.89% | 9.22% |
| found: | 76.71% | 10.52% | 4.08% | 8.84% | b): Under nitrogen, 100.69 g (0.28 mol) of 4-(hexadecylthio)benzonitrile (Example 1a) are added at 90° to a sodium tert-amylate solution, which is prepared from 9.66 g (0.42 mol) of sodium and 400 ml of t-amyl alcohol. With stirring, 28.32 g (0.14 mol) of diisopropyl succinate are then added over 6 hours at 102° C. The reaction mixture is stirred at 102° C. for another 16 hours and is then cooled to room temperature and forced into a mixture of 500 ml of water and 500 ml of methanol. This mixture is filtered and the filter product is washed with methanol and then with water. After drying at 80° C./160 mbar, 99.93 g (89.1% of theory) of a dark red product are obtained.

| Analysis: | C | H | N | S |
|---|---|---|---|---|
| calcd.: | 74.95% | 9.56% | 3.50% | 8.00% |
| found: | 75.11% | 9.78% | 3.63% | 8.11% | c): Under nitrogen, 9.62 g (0.012 mol) of the product of example 1b are added in small portions over 1 hour to a suspension consisting of 1.92 g (0.048 mol) of sodium hydride (60% dispersion in oil) in 200 ml of 1-methyl-2-pyrrolidone (dried over a molecular sieve). The reaction mixture is stirred for 1 hour at room temperature. With vigorous stirring, 6.81 g (0.048 mol) of methyl iodide are added dropwise to the solution so obtained. Stirring is continued for 50 hours and the mixture is then charged with 500 ml of an ice/water mixture and subsequently with 50 ml of ethyl acetate. The mixture is filtered and the filter product is rinsed with 2×20 ml of ethyl acetate. After extraction in a Soxhlet apparatus with 400 ml of dichloromethane, the extract is concentrated by evaporation and the residue is dried at 60° C./160 mbar, giving 3.73 g (37.5% of theory) of a red product of formula

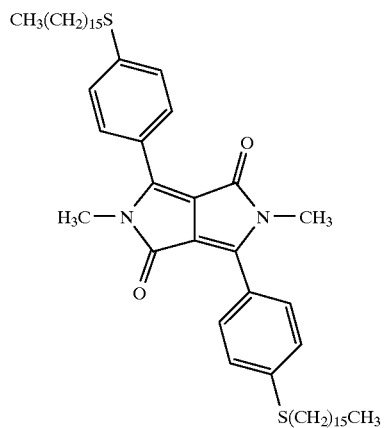

| Analysis: | C | H | N | S |
|---|---|---|---|---|
| calcd.: | 75.31% | 9.72% | 3.38% | 7.73% |
| found: | 75.14% | 9.97% | 3.53% | 7.55% |

The phase transition is determined by DSC. The texture of the mesophase is also seen under a polarising optical microscope:

cr.=90° C. (crystalline melting point: crystalline phase→liquid crystalline phase)

c.p.=114° C. (clearing point: liquid crystalline phase→isotropic liquid phase).

The liquid crystalline mesophase of this substance exists in the range of 90–114° C.

EXAMPLE 2 a) A suspension consisting of 75.66 g (0.55 mol) of 4-chlorobenzonitrile, 106.42 g (0.77 mol) of potassium carbonate and 111.32 g (0.55 mol) of 1-dodecanethiol is heated, with stirring, under an inert gas atmosphere in 280 ml of N,N-dimethylacetamide to 130° C. and is then stirred at this temperature for 24 hours. After cooling the reaction mixture to room temperature, it is poured on a mixture of 700 g of ice and 750 ml of water. The mixture is filtered and the filter cake is washed with water. The product is recrystallised from methanol and dried at 50° C. under vacuum, affording 160.2 g (96% of theory) of 4-(dodecyl-thio) benzonitrile.

| Analysis: | C | H | N | S |
|---|---|---|---|---|
| calcd.: | 75.19% | 9.63% | 4.62% | 10.56% |
| found: | 74.86% | 9.80% | 4.46% | 10.52% | b): Under nitrogen, 13.79 g (0.6 mol) of sodium are added to 400 ml of dry tert-amyl alcohol and this mixture is heated to 102° C. With vigorous stirring, the melted sodium is kept for 16 hours at 102° C. After cooling the resulting solution to 90° C., 121.4 g (0.4 mol) of 4-(dodecylthio)benzonitrile (of example 2a) are added. With stirring, 40.45 g (0.2 mol) of diisopropyl succinate are added to this mixture over 5¾ hours at 102° C. The reaction mixture is stirred at 102° C. for another 18 hours and is then cooled to room temperature and added to a mixture of 750 ml of methanol and 750 ml of water. The red suspension is filtered and washed first with methanol and then with water. The product is dried at 80° C.

under vacuum, giving 86.3 g (62.6% of theory) of a dark red powder.

| Analysis: | C | H | N | S |
|---|---|---|---|---|
| calcd.: | 73.21% | 8.78% | 4.07% | 9.31% |
| found: | 73.46% | 8.75% | 3.98% | 9.49% | c): Under nitrogen, 1.72 g (0.0025 mol) of the product of example 2b) are added to a suspension consisting of 0.40 g (0.010 mol) of sodium hydride (60% dispersion in oil) in 20 ml of 1-methyl-2-pyrrolidone (dried over a molecular sieve). After stirring this mixture for 1½ hours at room temperature, 1.42 g (0.010 mol) of methyl iodide are added dropwise and the reaction mixture is stirred for another 22 hours. Subsequently, the reaction mixture is poured on 100 ml of an ice/water mixture. 5 ml of ethyl acetate are added to the resulting emulsion. This mixture is filtered and the filter cake is washed with a small amount of ethyl acetate (about 5 ml). After a Soxhlet extraction with 300 ml of ethyl acetate, the solvent is stripped off under vacuum and the residue is dried at 60° C. under vacuum, affording 1.22 g (68% of theory) of a red product of formula

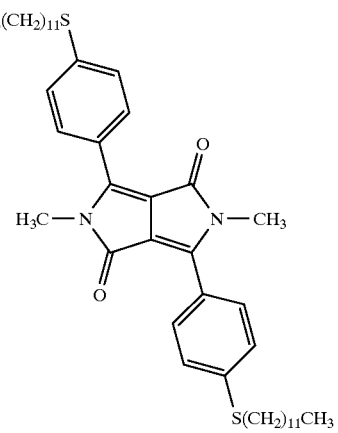

| Analysis: | C | H | N | S |
|---|---|---|---|---|
| calcd.: | 73.69% | 9.00% | 3.91% | 8.94% |
| found: | 73.56% | 9.00% | 3.90% | 8.74% |

The liquid crystalline mesophase of this substance exists in the range of 104–114° C.

EXAMPLE 3 a) Under nitrogen, a mixture consisting of 64.7 g (0.26 mol) of diethyl maleate and 0.4 g of dibenzoyl peroxide is added dropwise over 12½ hours to 104.9 g (0.81 mol) of caprylic aldehyde at 80° C. The reaction is completed by heating to 80° C. under nitrogen for 52 hours, adding another 0.4 g of dibenzoylperoxide in two equal portions. The reaction mixture is then cooled to room temperature, washed with saturated aqueous sodium carbonate solution and then dried over anhydrous magnesium sulfate. Fractional distillation affords 65.9 g (83% of theory) of diethyl α-octanoylsuccinate.

Melting point: 138–142° C./0.05 mbar.

| Analysis: | C | H |
|---|---|---|
| calcd.: | 63.97% | 9.40% |
| found: | 64.28% | 9.58% | b) 70.1 g of the product of example 3a) are added, with vigorous stirring, to a solution consisting of 137.5 g of ammonium acetate in 400 ml of acetic acid at 60° C. After stirring this mixture for another 20 hours under nitrogen at 100° C., it is cooled to room temperature and mixed with 600 ml of water. After extracting the resulting product with 300 ml of ethyl acetate, it is washed first with saturated aqueous sodium hydrogencarbonate solution and then with water and is subsequently dried over anhydrous magnesium sulphate. Purification by column chromatography gives 40.7 g (76.5% of theory) of a solid substance of formula

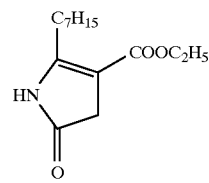

| Analysis: | C | H | N |
|---|---|---|---|
| calcd.: | 66.37% | 9.15% | 5.53% |
| found: | 64.73% | 9.21% | 5.11% | c) 50.09 g of caprylic acid nitrile are added at 90° C. under nitrogen to a sodium tert-amylate solution obtained from 6.9 g of sodium and 300 ml of tert-amyl alcohol. 25.33 g of the product of example 3b) are then added in portions to this mixture over 80 minutes at 80° C. and the reaction mixture is then stirred for 20 hours at reflux. After cooling the mixture to room temperature, it is mixed with 350 ml of water, 350 ml of methanol and 29.56 g of 37% hydrochloric acid and is then filtered. The residue is washed with water and dried at 80° C./160 mbar, giving 9.16 g (27.5% of theory) of a yellow product of formula

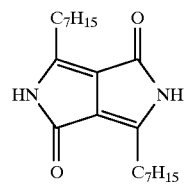

| Analysis: | C | H | N |
|---|---|---|---|
| calcd.: | 72.25% | 9.70% | 8.43% |
| found: | 72.11% | 9.83% | 8.39% | d) Under nitrogen, 3.99 g of the product of example 3c) are added in small portions at room temperature over 2½ hours to a suspension consisting of 1.92 g of sodium hydride in 60 ml of 1-methyl-2-pyrrolidinone. This mixture is stirred for 1 hour and then 6.81 g of methyl iodide are added dropwise over 50 minutes. After stirring the resulting suspension for 18 hours at room temperature under nitrogen, it is mixed with 120 ml of ice-cold water and extracted with ethyl acetate. The extraction product is dried over anhydrous magnesium sulphate and is then concentrated to dryness by evaporation. Purification of the remaining brown viscous liquid by column chromatography gives a yellow viscous product of formula

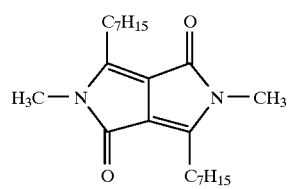

MS (EI): m/e 360 (M$^+$); c.p.: 66° C.

The liquid crystalline mesophase of this substance exists in the range of about 10 to 66° C. The SB mosaic texture of the mesophase is also seen under a polarising optical microscope.

EXAMPLES 4–8

A procedure analogous to that of examples 1 and 2 gives the following homologous compounds having liquid crystalline properties:

| Example | $R_{17}$ |
|---------|----------|
| 4 | $C_8H_{17}$ |
| 5 | $C_9H_{19}$ |
| 6 | $C_{10}H_{21}$ |
| 7 | $C_{14}H_{29}$ |
| 8 | $C_{18}H_{37}$ |

EXAMPLES 9–16

A procedure analogous to that of examples 1 and 2 gives the following homologous compounds having liquid crystalline properties:

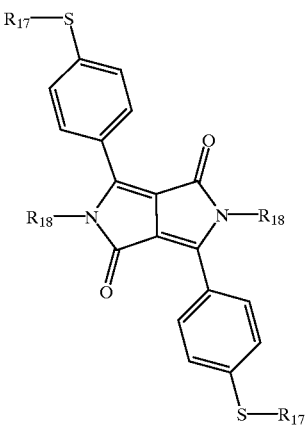

| Example | $R_{17}$ | $R_{18}$ |
|---------|----------|----------|
| 9 | $C_8H_{17}$ | $C_{12}H_{25}$ |
| 10 | $C_9H_{19}$ | $C_{12}H_{25}$ |
| 11 | $C_{10}H_{21}$ | $C_{16}H_{33}$ |
| 12 | $C_{12}H_{25}$ | $C_{12}H_{25}$ |
| 13 | $C_{12}H_{25}$ | $C_{16}H_{33}$ |
| 14 | $C_{14}H_{29}$ | $C_{18}H_{37}$ |
| 15 | $C_{16}H_{33}$ | $C_{18}H_{37}$ |
| 16 | $C_{18}H_{37}$ | $C_{18}H_{37}$ |

EXAMPLE 17 a) 4.0 g of sodium are stirred in 200 ml of tert-amyl alcohol at reflux temperature until the reaction is complete. After cooling to 90° C., 51.94 g of 3,4-di-decyl-thiobenzonitrile are added, followed by the dropwise addition of 11.73 g of diisopropyl succinate. The resulting violet coloured reaction mixture is heated to reflux and stirred overnight. It is then cooled to room temperature, transferred to a well-stirred water-methanol mixture and stirred for a further 4 hours. The crude product is collected by filtration and reslurried in a methanol-ethyl acetate mixture. The resultant product crystals are filtrated, washed with methanol and dried at 50° C./160 mbar, affording 28.27 g (49.8% of theory) of the compound of formula

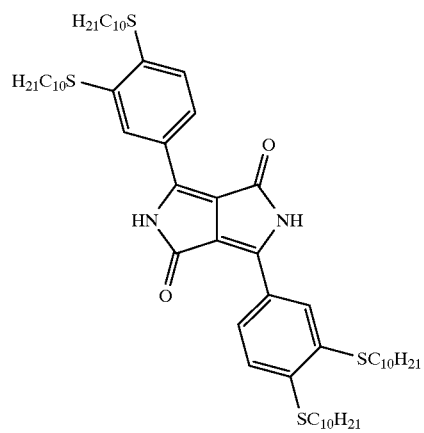

| Analysis:   | C      | H     | N     | S      |
|-------------|--------|-------|-------|--------|
| calculated: | 71.26% | 9.48% | 2.87% | 13.12% |
| found:      | 70.89% | 9.54% | 2.91% | 13.12% | b): 24.44 g of the product of example 17a) are added, in small portions, to a well stirred mixture of 4.0 g of sodium hydride (60% dispersion in mineral oil) and 300 ml of 1-methyl-2-pyrrolidinone under nitrogen atmosphere. After stirring for 75 minutes, 14.19 g of methyl iodide is added, and the reaction is allowed to proceed at room temperature overnight. The mixture is then poured into an ice-water mixture, the precipitated product is filtered off, washed with water and dried at 50° C. under vacuum. The crude product is recrystallised from ethyl acetate to yield 11.06 g (44% of theory) of a bright red coloured crystalline product of the formula

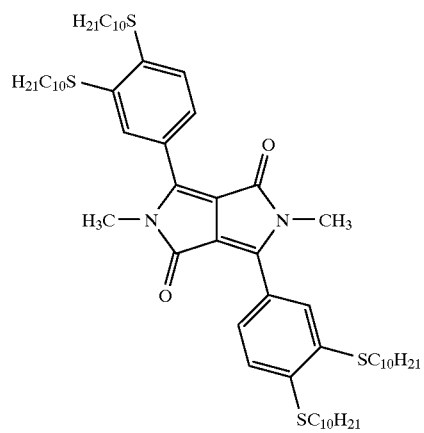

| Analysis:   | C      | H     | N     | S      |
|-------------|--------|-------|-------|--------|
| calculated: | 71.66% | 9.62% | 2.79% | 12.75% |
| found:      | 71.70% | 9.61% | 2.85% | 12.83% |

$^1$H-NMR(CDCl$_3$): 7.88 (s, 2H); 7.69 (d, 2H); 7.30 (d, 2H); 3.37 (s, 6H); 3.07–2.97 (m, 8); 1.78–1.67 (m, 8H); 1.53–1.40 (m, 8H); 1.35–1.20 (m, 48H); 0.91–0.84 (m, 12H).

EXAMPLE 18 a) A suspension of 122.80 g of 4-hydroxybenzonitrile in 458 ml of 3,4-dihydro- 2H-pyran is stirred at reflux temperature for 72 hours, after which the excess of the solvent is evaporated off under reduced pressure. The resultant yellow coloured oil is purified by flash column chromatography (silica gel, n-hexane/ethyl acetate, 9:1) to yield 179.05 g (88.1% of theory) of a colourless crystalline compound of the formula

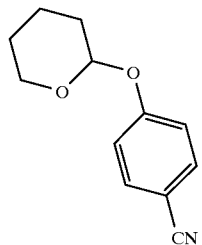

| Analysis:   | C      | H     | N     |
|-------------|--------|-------|-------|
| calculated: | 70.92  | 6.45  | 6.89  |
| found:      | 70.91  | 6.72  | 6.74  | b): Under nitrogen atmosphere, 89.43 g of the product of example 18a) are added to a sodium tert-amyl alcohol solution heated to 90° C., followed by the dropwise addition of 53.40 g of diisopropyl succinate over 1½ hours. The reaction mixture is stirred for 24 hours under reflux and then cooled down to room temperature. It is transferred to a water-methanol mixture, and the resultant red mixture heated to 60° C. and stirred at this temperature for 4½ hours. The solid is collected by filtration, washed with water and dried at 80° C. under vacuum, affording 12.25 g (11.4% of theory) of the compound of formula

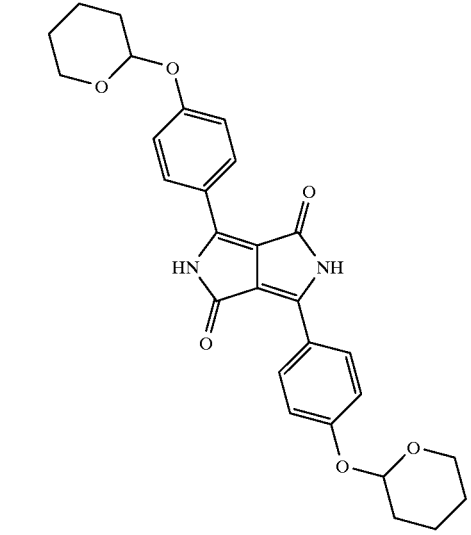

| Analysis:   | C      | H     | N     |
|-------------|--------|-------|-------|
| calculated: | 68.84% | 5.78% | 5.73% |
| found:      | 68.15% | 6.05% | 5.72% | c): A mixture of 48.85 g of the product of example 18b), 1 l of ethanol, 63 ml of water and 5.6 ml of concentrated sulphuric acid is heated and stirred at reflux for 25 hours. After cooling to room temperature, the precipitated product is collected by filtration, washed with ethanol and water and dried at 80° C. under vacuum, affording 20 g (62.5% of theory) of the product of formula

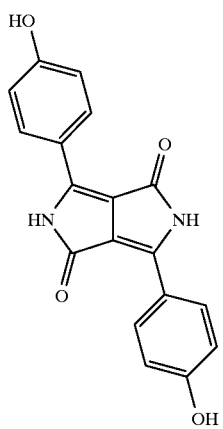

| Analysis: | C | H | N |
|---|---|---|---|
| calculated: | 67.50% | 3.78% | 8.75% |
| found: | 63.89% | 4.08% | 8.33% | d): 9.61 g of the product of example 18c) are added in small portions to a well stirred mixture of 9.6 g of sodium hydride (60% dispersion in mineral oil) and 200 ml of 1-methyl-2-pyrrolidinone under nitrogen atmosphere. After stirring for 1 hour, 71.10 g of 1-iodododecane are added during a period of 30 minutes, and the reaction is allowed to proceed at room temperature for 27½ hours. The reaction mixture is diluted with 500 ml of water, and the product isolated by filtration, recrystallised from ethyl acetate to yield 6.40 g (21.5% of theory) of the compound of formula

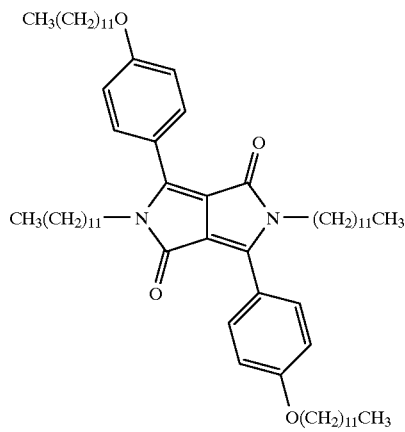

| Analysis: | C | H | N |
|---|---|---|---|
| calculated: | 79.78% | 10.96% | 2.82% |
| found: | 79.67% | 10.82% | 2.78% |

EXAMPLE 19 a) A sodium tert-amylate solution is prepared by reacting 10.12 g of sodium with 450 ml of tert-amyl alcohol at reflux temperature overnight. It is then cooled to 90° C. and 63.24 g of 4-dodecyloxybenzonitrile are added, followed by the dropwise addition of 22.24 g of diisopropyl succinate over 5 hours. The reaction mixture is stirred for 21 hours under reflux and then allowed to cool down to room temperature. It is transferred into a water-methanol mixture and the precipitated product collected by filtration, rinsed with methanol and water, and dried at 80° C. under vacuum. This affords 6.90 g (9.55% of theory) of the compound of formula

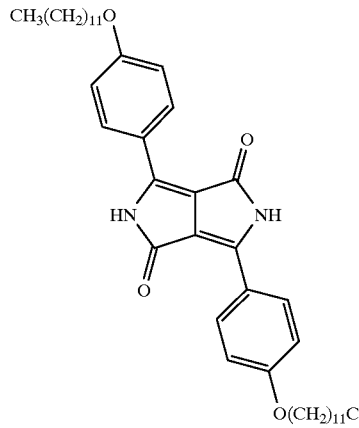

| Analysis: | C | H | N |
|---|---|---|---|
| calculated: | 76.79% | 9.21% | 4.26% |
| found: | 76.24% | 8.96% | 4.11% | b): 9.85 g of the compound from example 19a) are added to a mixture of 2.40 g of sodium hydride (60% dispersion in mineral oil) in 200 ml of 1-methyl-2-pyrrolidinone, under nitrogen atmosphere, and the mixture is stirred at room temperature for 1½ hours, resulting in a violet coloured solution. 8.52 g of iodomethane are added portionwise to this well-stirred solution, and the suspension is stirred at ambient temperature for 24 hours. It is then poured into an ice-water mixture, the precipitated product is isolated by filtration, washed with water and dried at 80° C. under vacuum, affording 9.76 g of the compound of formula

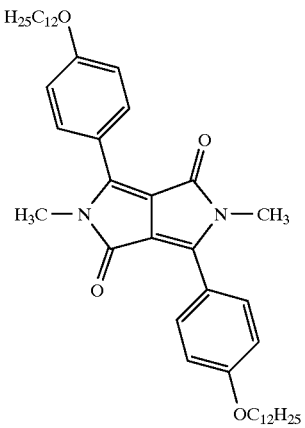

A crystalline sample is obtained by recrystallisation from ethyl acetate.

| Analysis:   | C      | H     | N     |
|-------------|--------|-------|-------|
| calculated: | 77.15% | 9.42% | 4.09% |
| found:      | 76.87% | 9.48% | 4.10% |

| Analysis:   | C      | H     | N     |
|-------------|--------|-------|-------|
| calculated: | 82.34% | 9.71% | 4.18% |
| found:      | 82.35% | 8.52% | 4.08% |

EXAMPLES 20–29

A procedure analogous to that of example 19 gives the following homologous compounds having liquid crystalline properties:

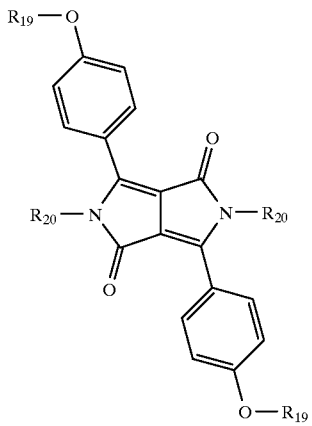

| Example | $R_{19}$ | $R_{20}$ |
|---------|----------|----------|
| 20 | $C_7H_{15}$ | $CH_3$ |
| 21 | $C_9H_{19}$ | $CH_3$ |
| 22 | $C_{10}H_{21}$ | $CH_3$ |
| 23 | p-$H_5C_2OC_2H_4OC_6H_4$— | $CH_3$ |
| 24 | p-$H_{21}C_{10}C_6H_4$— | $CH_3$ |
| 25 | $C_7H_{15}$ | $C_{10}H_{21}$ |
| 26 | $C_9H_{19}$ | $C_{10}H_{21}$ |
| 27 | $C_9H_{19}$ | $C_{12}H_{25}$ |
| 28 | $C_{12}H_{25}$ | $C_{12}H_{25}$ |
| 29 | $C_{12}H_{25}$ | $C_{16}H_{33}$ |

EXAMPLE 30 a) An aqueous sodium hydroxide solution (2.24 g in 20 ml water) is added to a solution of 10.0 g of 4'-hydroxy-4-biphenylcarbonitrile in 250 ml ethanol at 50° C., under nitrogen atmosphere, followed by 28.3 g of 1-bromodecane added dropwise over 20 minutes. The resulting yellow coloured suspension is stirred at 60° C. for 26 hours, then chilled in an ice bath. The precipitate is collected by filtration, rinsed with cold ethanol and dried at 30° C. under vacuum. This yields 12.48 g (72.9% of theory) of a white crystalline compound of the formula

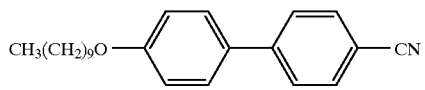

b): Under nitrogen atmosphere, 12.18 g of the product of example 30a) are added to a sodium tert-amyl alcohol solution heated to 100° C., followed by the dropwise addition of 3.67 g of diisopropyl succinate. The reaction mixture is stirred for 16 hours under reflux, then cooled to room temperature and transferred to a mixture containing 250 ml of methanol, 9 ml of acetic acid and 150 ml of tert-amyl alcohol. The resultant suspension is stirred at ambient temperature for 3 hours. The product is collected by filtration, washed with methanol, then with water, and dried at 80° C. under vacuum, affording 8.42 g (61.6% of theory) of the compound of formula

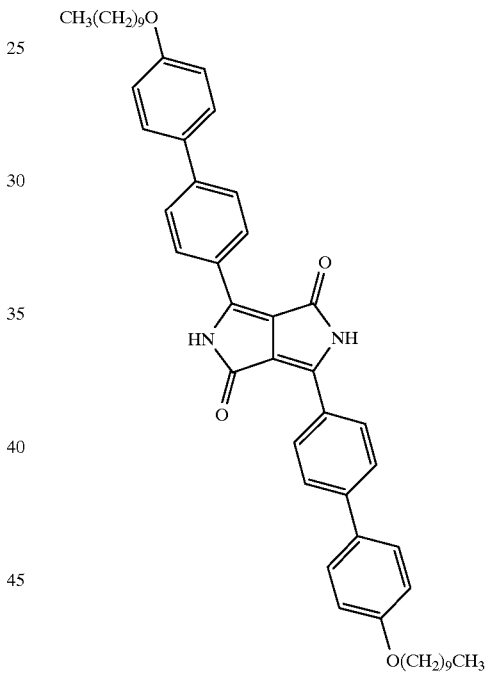

| Analysis:   | C      | H     | N     |
|-------------|--------|-------|-------|
| calculated: | 79.75% | 8.03% | 3.72% |
| found:      | 79.01% | 7.97% | 3.47% | c): 8.28 g of the product of example 30b) and 25 ml of tert-amyl alcohol are added under nitrogen atmosphere to a sodium tert-amylate solution (prepared with 0.56 g sodium and 80 ml tert-amyl alcohol) at 100° C. The mixture is stirred for 2 hours at the reflux temperature, then cooled to room temperature, and 3.88 g of dimethyl sulphate are added portionwise over a period of 30 minutes. The resulting mixture is stirred at room temperature for 48 hours during which 1.94 g more dimethyl sulphate is added. The product is collected by filtration, washed with methanol and dried under vacuum. The crude product is extracted into methylene chloride in a Soxhlet, and the extract is evaporated to dryness. Recrystallization from ethyl acetate affords 3.77 g (43.9%) of the compound of formula

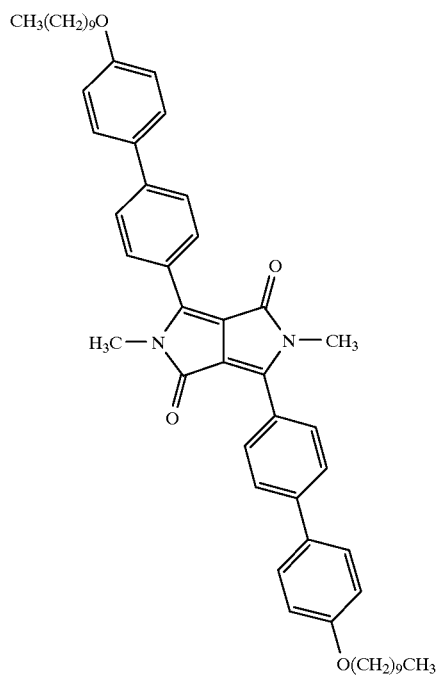

| Analysis: | C | H | N |
|---|---|---|---|
| calculated: | 79.96% | 8.26% | 3.59% |
| found: | 79.48% | 8.27% | 3.48% |

Melting point 139.3° C.; clearing point 302.9° C.

Under an optical polarizing microscope, the Schlieren texture of the nematic mesophase is observed.

EXAMPLE 31

Following the synthetic procedure described in example 30, the following liquid crystalline compound is obtained by using 1-iodohexadecane instead of 1-bromodecane:

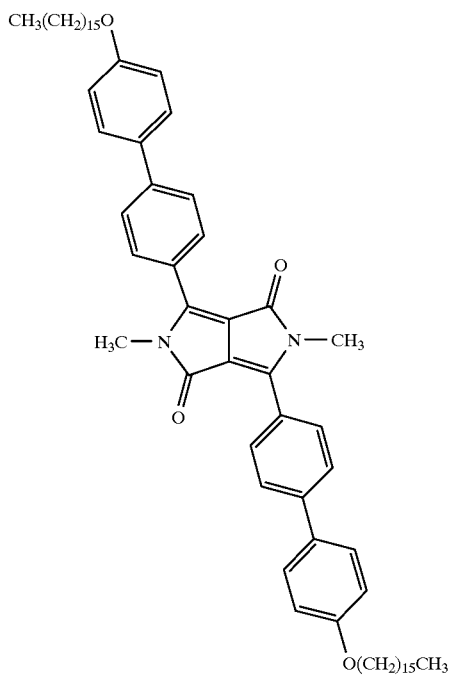

| Analysis: | C | H | N |
|---|---|---|---|
| calculated: | 80.97% | 9.34% | 2.95% |
| found: | 80.96% | 9.44% | 2.81% |

Melting point 115.8° C.; clearing point 234.5° C. Under an optical polarizing microscope, the Schlieren texture of the nematic mesophase is observed.

EXAMPLE 32 a) The general procedure of example 18a) is repeated, but replacing 4-hydroxybenzonitrile with 3,5-dihydroxybenzonitrile. The following compound is obtained:

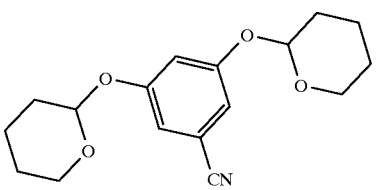

b): Following the synthetic procedure described in example 18b) but using the benzonitrile from example 32a) instead, the following compound is obtained:

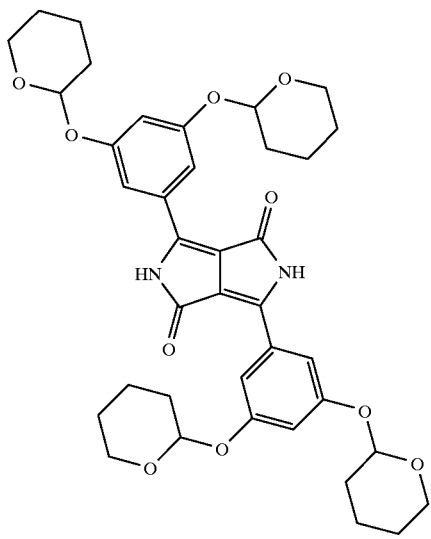

| Analysis: | C | H | N |
|---|---|---|---|
| calculated: | 66.26% | 6.44% | 4.07% |
| found: | 65.52% | 6.51% | 4.08%. | c): The general procedure of example 19b) is repeated, using the product of example 32b) instead of that of example 19a), and replacing iodomethane with 1-iododecane. The following compound is obtained:

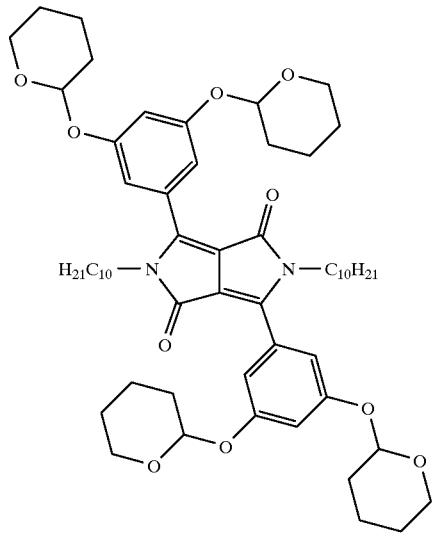

The ¹H-NMR spectrum confirms the structure.

EXAMPLE 33 a) The product of example 32c) is subjected to acid hydrolysis following the general procedure analogous to example 18c), yielding the following compound:

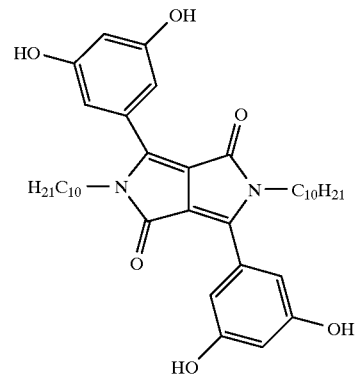

The ¹H-NMR spectrum is in full agreement with the structure.

b): The general procedure of example 18d) is repeated, but using the product of example 33a) instead of that of example 18c), and replacing 1-iodododecane with 1-iodoheptane, giving the following compound having liquid crystalline properties:

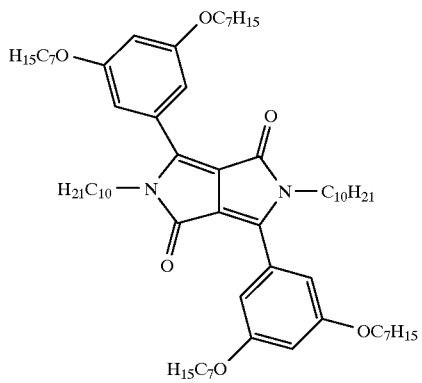

| Analysis: | C | H | N |
|---|---|---|---|
| calculated: | 77.29% | 10.61% | 2.73% |
| found: | 77.00% | 11.20% | 2.32% |

EXAMPLE 34 a) 53 g of 4-cyanobenzaldehyde, 34.5 ml of 1,3-propanediol, 9.19 g of tosyl acid and 1 l benzene are placed in a flask equipped with a stirrer and a Dean-Stark separator fitted with a condenser. The mixture is stirred under reflux for 5 hours, during which approximately 7 ml of water are collected in the trap. The resulting mixture is cooled to room temperature and extracted first with a 2% aqueous sodium hydrogencarbonate solution (2×500 ml), and then with distilled water (2×500 ml). The organic phase is dried over MgSO$_4$. The solvent is removed under reduced pressure and the solid dried under vacuum at 60° C. 68.2 g (90.1% of theoretical) of the following compound are obtained:

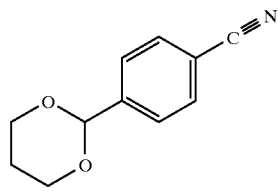

The white crystalline solid has a melting point of 108–109° C.

| Analysis:   | C      | H     | N     |
|-------------|--------|-------|-------|
| calculated: | 69.83% | 5.86% | 7.40% |
| found:      | 69.88% | 5.87% | 7.10% | b): 37.8 g of the product of example 34a), followed by 20.2 g of di-isopropyl succinate, are added to a sodium tert-amylate solution, obtained from 6.90 g of sodium and 600 ml of tertamyl alcohol, under nitrogen. After heating up to 100° C., the reaction is allowed to continue at this temperature for 28 hours. After that, the mixture is cooled to room temperature and poured into a mixture of 45 ml acetic acid and 1400 ml methanol. The fine crystalline product is collected by filtration, washed with methanol followed by water, and dried under vacuum at 80° C. This yields 18.0 g (39% of the theoretical) of a dark red solid product with the following structure:

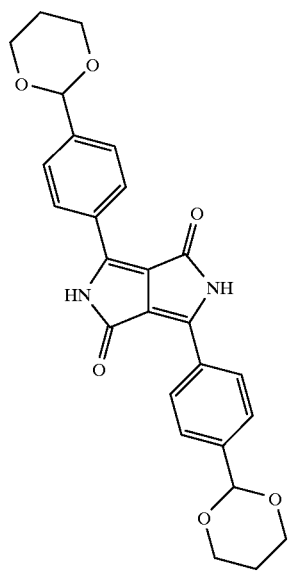

| Analysis:   | C      | H     | N     |
|-------------|--------|-------|-------|
| calculated: | 67.82% | 5.25% | 6.08% |
| found:      | 67.71% | 5.29% | 6.07% | c): A suspension of 6.70 g of the product of example 34b), 300 ml of a 2M aqueous hydrochloric acid solution and 350 ml of tetrahydrofuran is stirred under reflux for 70 hours and then cooled to room temperature. The dark red product is collected by filtration, washed with methanol and water, and dried under vacuum at 60° C. This yields 4.86 g (97% of the theoretical) of a product with the following structure:

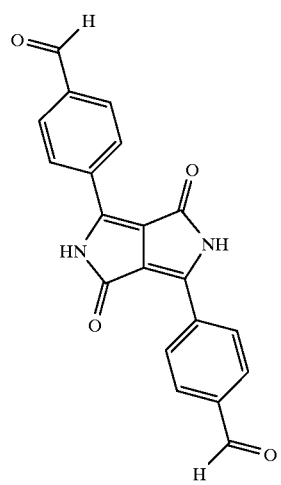

| Analysis:   | C      | H     | N     |
|-------------|--------|-------|-------|
| calculated: | 69.76% | 3.51% | 8.14% |
| found:      | 68.58% | 3.66% | 8.09% | d): A mixture of 1.00 g of the product of example 34c), 1.54 g of p-octyloxyaniline, 0.08 g of p-tosyl acid and 50 ml of methyl sulfoxide is stirred at 110° C. for 3 hours. It is then cooled to ambient temperature and left overnight. The solid product is collected by filtration, washed with methanol and water, and dried under vacuum at 60° C., yielding 1.94 g (89% of the theory) of a dark red crystalline compound of the formula:

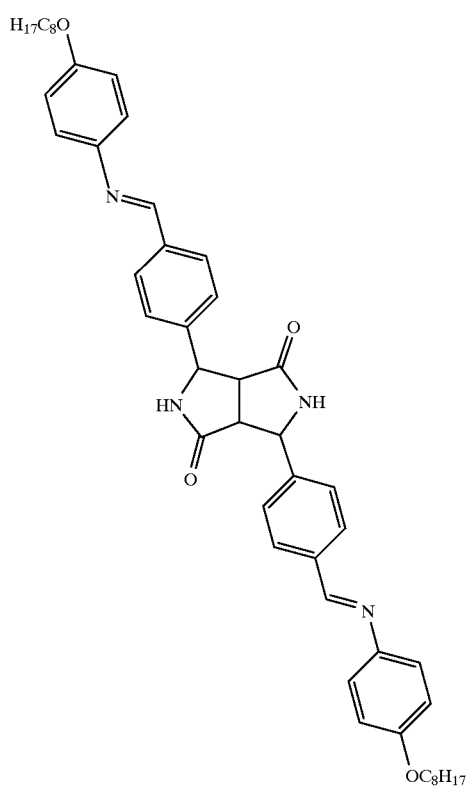

| Analysis: | C | H | N |
|---|---|---|---|
| calculated: | 76.77% | 7.25% | 7.46% |
| found: | 76.01% | 7.06% | 7.56% | e): The general procedure of example 19b) is repeated, but using the product of example 34d) instead of that of example 19a), yielding the following compound with liquid crystalline properties:

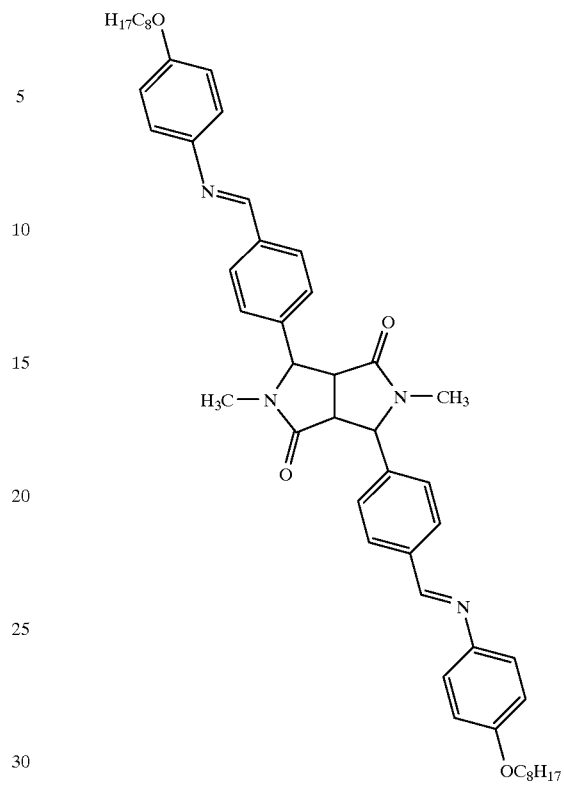

| Analysis: | C | H | N |
|---|---|---|---|
| calculated: | 77.09% | 7.50% | 7.19% |
| found: | 76.38% | 7.30% | 7.27% |

EXAMPLE 35 a) The general procedure of example 34a) is repeated, but replacing 1,3-propanediol with 1,2-tetradecanediol, giving the following compound:

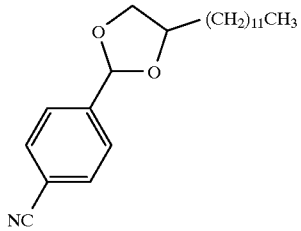

| Analysis: | C | H | N |
|---|---|---|---|
| calculated: | 76.92% | 9.68% | 4.08% |
| found: | 76.37% | 10.07% | 3.49% | b): The general procedure of example 34b) is repeated, but using the benzonitrile from example 35a) instead of that from example 34a). A dark red product is obtained.

| Analysis: | C | H | N |
|---|---|---|---|
| calculated: | 74.96% | 8.91% | 3.64% |
| found: | 74.89% | 9.09% | 3.39% | c): The general procedure of example 19b) is followed, using the product of example 35b) instead of that of example 19a), yielding the following compound useful in liquid crystalline compositions:

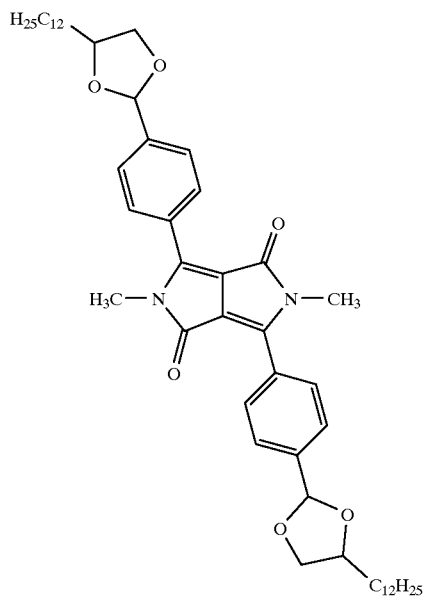

EXAMPLES 36–40

A procedure analogous to that of example 3 gives the following homologous compounds having liquid crystalline properties:

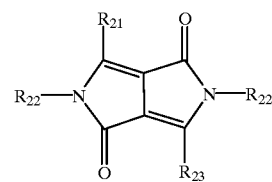

| Example | $R_{21}$ | $R_{22}$ | $R_{23}$ |
|---|---|---|---|
| 36 | $C_7H_{15}$ | $C_7H_{15}$ | $C_7H_{15}$ |
| 37 | $C_6H_{13}$ | $CH_3$ | p-Cl—$C_6H_4$— |
| 38 | $C_6H_{13}$ | $C_6H_{13}$ | p-Cl—$C_6H_4$— |
| 39 | $C_7H_{15}$ | $CH_3$ | p-Cl—$C_6H_4$— |
| 40 | $C_7H_{15}$ | $C_7H_{15}$ | p-Cl—$C_6H_4$— |

EXAMPLES 41–49

Following the procedure of the above examples, or in close analogous thereto, one obtains the following compounds of formula IIc having liquid crystalline properties observable under a polarising optical microscope:

| Ex. | $R_{14}$ | L | cr. [° C.] | [kJ/mol] | mesophase | c.p. [° C.] |
|---|---|---|---|---|---|---|
| 19 | $OC_{12}H_{25}$ | $CH_3$ | 108 | 82 | smectic A | 122 |
| 22 | $OC_{10}H_{21}$ | $CH_3$ | 106 | 69 | smectic A | 118 |
| 41 | $OC_8H_{17}$ | $CH_3$ | 106 | 59 | nematic | 114 |
| 42 | —⟨C₆H₄⟩—$OC_6H_{13}$ | $CH_3$ | 205 | 44 | nematic | 336 |
| 43 | —⟨C₆H₄⟩—$C_4H_9$ | $CH_3$ | 220 | 4 | nematic | 331 |

-continued

| Ex. | R₁₄ | L | cr. [° C.] | [kJ/mol] | mesophase | c.p. [° C.] |
|---|---|---|---|---|---|---|
| 44 | —⟨cyclohexyl⟩-‴C₃H₇ | CH₃ | 190 | 23 | nematic | 357 |
| 45 | —⟨phenyl⟩-⟨cyclohexyl⟩-‴C₅H₁₁ | CH₃ | 248 | 31 | nematic | 327 |
| 46 | —⟨phenyl⟩-⟨cyclohexyl⟩-‴C₅H₁₁ | C₂H₅ | 243 | 38 | nematic | 348 |
| 47 | —⟨phenyl⟩-⟨cyclohexyl⟩-‴C₅H₁₁ | C₃H₇ | 210 | 36 | nematic | 337 |
| 48 | —⟨dioxane⟩-C₅H₁₁ | CH₃ | 182 | 20 | LC range narrow | |
| 49 | —⟨phenyl⟩-OC₁₄H₂₉ | CH₃ | 137 | 32 | smectic | 280 |

EXAMPLES 50–52

A procedure analogous to that of the above examples gives the compounds of formula IIa having liquid crystalline properties, which compounds are observed under the polarisation microscope at rising temperature:

| Ex. | R₁₃ = R₁₄ = R₁₅ | L | cr. [° C.] | [kJ/mol] | mesophase⁽ˡ⁾ | c.p. [° C.] |
|---|---|---|---|---|---|---|
| 50 | OC₆H₁₃ | CH₃ | 117 | 36 | columnar | 146 |
| 51 | OC₈H₁₇ | CH₃ | 83 | 32 | columnar | 129 |
| 52 | OC₁₀H₂₁ | CH₃ | 65 | 45 | columnar | 114 |

⁽ˡ⁾these mesophases may also be smectic instead of columnar.

EXAMPLE 53

A binary mixture of the compounds of examples 41 and 46 (1:1 by weight) exhibits liquid crystalline properties observable under the polarising optical microscope:

| Ex. | R₁₄ | L | cr. [° C.] | [kJ/mol] | mesophase⁽†⁾ | c.p. [° C.] |
|---|---|---|---|---|---|---|
| 53 | —⟨phenyl⟩-⟨cyclohexyl⟩-‴C₅H₁₁ —OC₈H₁₇ | CH₃ CH₃ | 138 | 19 | nematic | 280 |

⁽†⁾this mesophase may also be smectic instead of nematic.

EXAMPLE 54

A binary mixture of the compound of example 41 and the compound of formula

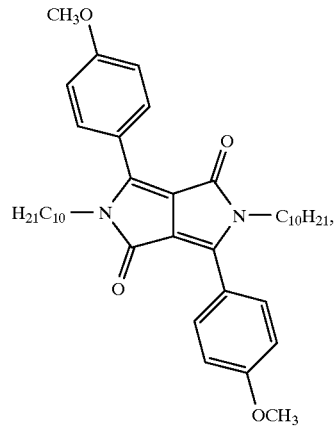

which is prepared according to the above examples (3:1 by weight), exhibits liquid crystalline properties.

EXAMPLE 55

A binary mixture of the compound of example 41 and the compound of formula IIc, wherein L is methyl and R₁₄ is

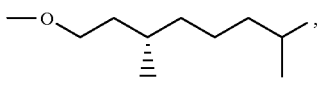

which is prepared in analogy thereto, (3:1 by weight), exhibits liquid crystalline properties.

EXAMPLES 56

5% by weight of the compound of example 12 are mixed with 95% by weight of the liquid crystalline compound of formula

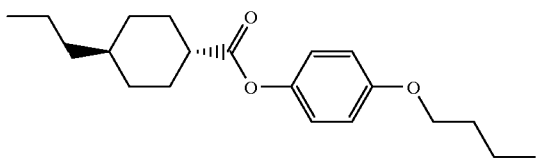

The binary mixture's colour contrast and order parameter are high.

EXAMPLE 57

5% by weight of the compound of example 12 are mixed with 95% by weight of the liquid crystalline compound (NBBA) of formula

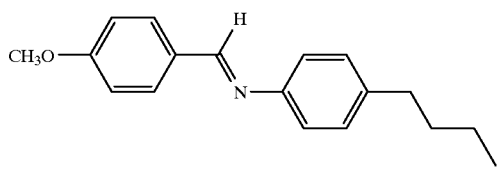

The binary mixture's colour contrast and order parameter are high.

What is claimed is:

1. A compound of formula

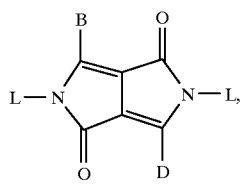 (I)

wherein

B and D are each independently of the other $C_6$–$C_{24}$alkyl,

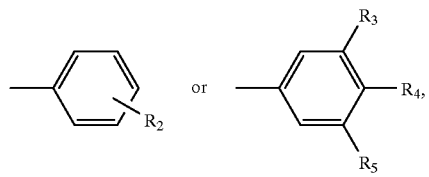

L is

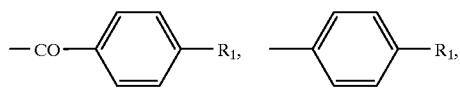

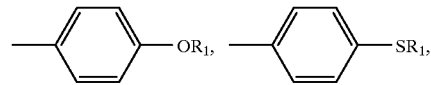

methyl or straight-chain $C_{10}$–$C_{18}$ alkyl, with the proviso that when L is methyl, at least one of B and D is $C_6$–$C_{24}$ alkyl, $R_1$ is $C_4$–$C_{18}$alkyl, $R_2$ is hydrogen, $C_1$–$C_4$alkyl, $C_1$–$C_4$alkoxy, halogen, cyano or nitro, R3, R4 and R5 are each independently of one another hydrogen, $OR_6$, $SR_6$, $SeR_6$, —$NHR_6$, —$NR_6R_7$,

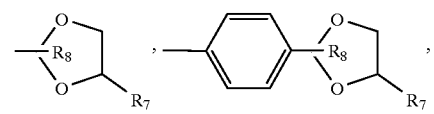

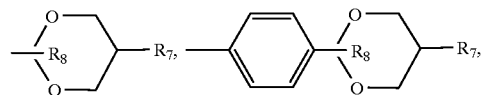

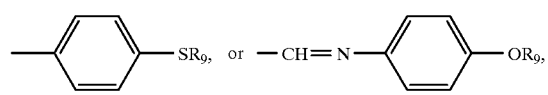

with the proviso that at least one of $R_3$, $R_4$ and $R_5$ is not hydrogen, $R_6$ is $C_7$–$C_{37}$alkyl, $C_7$–$C_{37}$alkylene, or $C_5$–$C_{18}$alkyl which is interrupted by 1 to 6 hereto atoms selected from the group consisting of O, S and N, $R_7$ is hydrogen or $R_9$, $R_8$ is hydrogen or $C_1$–$C_4$alkyl, and $R_9$ is $C_1$–$C_{12}$alkyl, $C_2$–$C_{12}$alkylene, or $C_3$–$C_{12}$alkyl which is interrupted by 1 to 6 hereto atoms which are selected from the group consisting of O, S and N.

2. A compound of formula I according to claim 1, wherein L is methyl, straight-chain $C_{10}$–$C_8$-alkyl or

and $R_1$ is $C_6$–$C_{12}$alkyl.

3. A compound of formula I according to claim 1, wherein B is $C_6$–$C_{24}$alkyl and L is methyl.

4. A compound of formula I according to claim 1, wherein B and D are identical.

5. A compound of formula I according to claim 1, wherein B and D are straight-chain $C_6$–$C_{10}$alkyl,

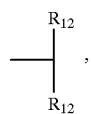

wherein $R_{12}$ and $R_{12}'$ are straight-chain $C_{10}$–$C_{14}$alkyl,

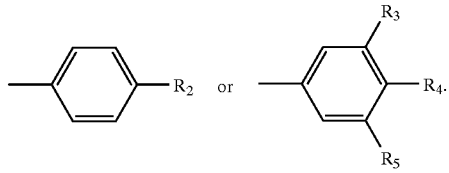

6. A compound according to claim 5, wherein B and D are

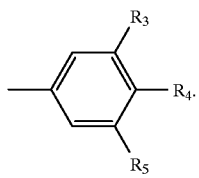

7. A compound according to claim 6, wherein $R_3$, $R_4$ or $R_5$ other than hydrogen is $OR_6$ or $SR_6$, and $R_6$ is straight-chain $C_{10}$–$C_{24}$alkyl or

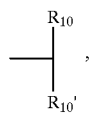

wherein $R_{10}$ and $R_{10}'$ are each independently of the other straight-chain $C_{10}$–$C_{18}$alkyl.

8. A compound according to claim 1 of formula IIa, IIb, IIc or IId,

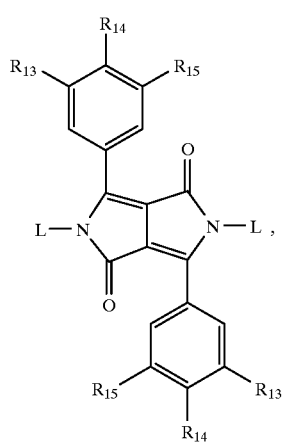
(IIa)

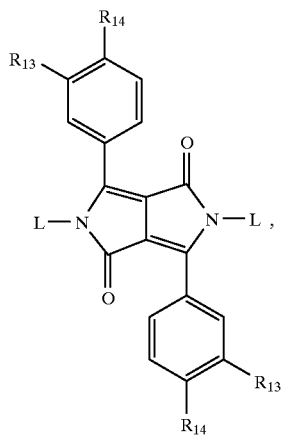
(IIb)

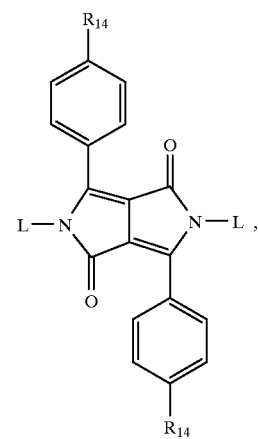
(IIc)

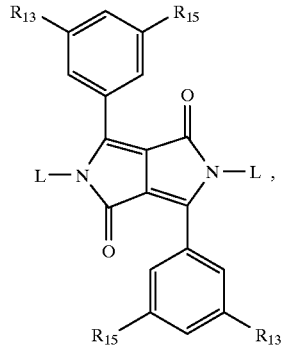
(IId)

wherein $R_{13}$, $R_{14}$ and $R_{15}$ are each independently of one another $OR_6$, $SR_6$, $SeR_6$, —$NHR_6$,

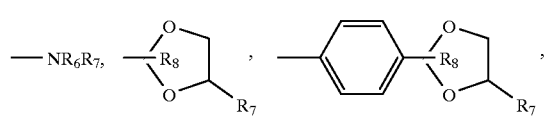

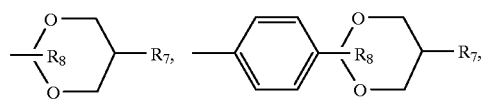

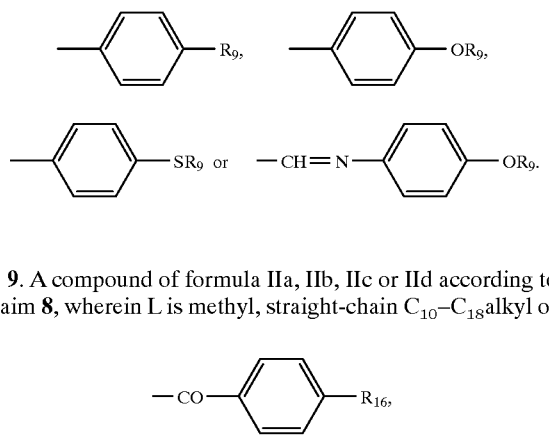

9. A compound of formula IIa, IIb, IIc or IId according to claim 8, wherein L is methyl, straight-chain $C_{10}$–$C_{18}$alkyl or $R_{16}$, $R_6$ is straight-chain $C_{10}$–$C_{18}$alkyl, and $R_{16}$ is straight-chain $C_6$–$C_{12}$alkyl.

10. A compound according to claim 8, which is of formula IIa, IIb or IId, wherein L is $C_{10}$–$C_{18}$ alkyl and $R_{13}$ and/or $R_{15}$ are $OR_6$, $SR_6$, $NHR_6$ or $NR_6R_7$.

11. A compound according to claim 10, having a liquid crystalline phase.

12. A compound according to claim 11, which is discotic.

13. A compound according to claim 12, having a nematic liquid crystalline phase.

14. A compound according to claim 13, further having a smectic liquid crystalline phase.

15. A compound according to claim 8, wherein $R_{13}$ and $R_{15}$ are S—($C_8$–$C_{16}$) alkyl.

16. A compound according to claim 10, wherein $R_{13}$ and $R_{15}$ are S—($C_8$–$C_{16}$) alkyl.

* * * * *